United States Patent [19]

Nakagawa et al.

[11] 4,378,355

[45] Mar. 29, 1983

[54] FUNGICIDAL COMPOSITION FOR AGRICULTURE AND HORTICULTURE AND ITS USE

[75] Inventors: Taizo Nakagawa, Ageo; Kaoru Ohmori, Okagawa, both of Japan

[73] Assignee: Nippon Kayaku Kabushiki Kaisha, Tokyo, Japan

[21] Appl. No.: 289,143

[22] Filed: Aug. 3, 1981

[51] Int. Cl.³ .................. A61N 31/18; A61N 37/34; A61N 37/36

[52] U.S. Cl. .................. 424/230; 424/304; 424/349

[58] Field of Search .................. 424/230, 304, 349

[56] References Cited

U.S. PATENT DOCUMENTS 2,887,433  5/1959  Swank .................. 424/349
3,456,055  7/1969  Galloway .................. 424/304
4,200,632  4/1980  Nakagawa et al. .................. 424/230
4,303,668  12/1981  Hasegawa et al. .................. 424/304

*Primary Examiner*—Stanley J. Friedman
*Assistant Examiner*—John W. Rollins, Jr.
*Attorney, Agent, or Firm*—Henry C. Nields

[57] ABSTRACT

The present invention relates to a fungicidal composition for agriculture and horticulture comprising at least one adjuvant and, as an effective component, in effective amounts, N-(1-n-butoxy-2,2,2-trichloroethyl) salicylamide and one member selected from the group consisting of (1) pentachloronitrobenzene and (2) tetrachloroisophthalonitrile.

This composition is useful to control soil borne plant diseases such as clubroot disease of Cruciferae crops, black scurf of potatoes and damping-off of cucumber and tomato seedlings.

4 Claims, No Drawings

FUNGICIDAL COMPOSITION FOR AGRICULTURE AND HORTICULTURE AND ITS USE

DETAILED DESCRIPTION OF THE INVENTION

The present invention relates to a fungicidal composition for agriculture and horticulture comprising at least one adjuvants and, as an effective component, in effective amounts, N-(1-n-butoxy-2,2,2-trichloroethyl) salicylamide

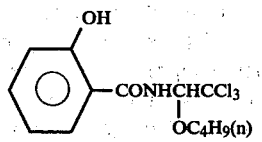

and one member selected from the group consisting of (1) pentachloronitrobenzene

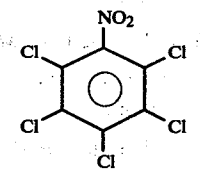

and (2) tetrachloroisophthalonitrile

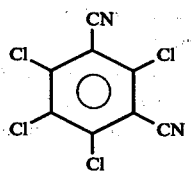

This composition is useful to control soil borne plant diseases such as clubroot disease of Cruciferae crops, black scurf of potatoes and damping-off of cucumber and tomato seedlings.

N-(1-n-butoxy-2,2,2-trichloroethyl) salicylamide (hereinafter referred to as "compound A"), one of the effective components of the present invention is a known compound described in the specification of U.S. Pat. No. 4,200,632. This compound is highly effective for controlling soil borne plant diseases, particularly clubroot disease of Cruciferae crops. However, when the compound is used at a low concentration, a sufficient fungicidal effect cannot always be obtained on plant diseases caused by Rhizoctonia sp. and the like.

Pentachloronitrobenzene (hereinafter referred to as "PCNB") is now available on the market as a fungicide against clubroot disease of Cruciferae crops and black scurf of potatoes. Though the compound is effective against the fungi of Plasmodiophora sp. and Rhizoctonia sp., there is a problem of the residual toxicity since it is used in a large amount.

Tetrachloroisophthalonitrile (hereinafter referred to as "TPN") is now available on the market as a fungicide for controlling clubroot disease of Cruciferae crops and damping-off of cucumber and tomato seedlings. However, the sufficient controlling effect cannot be obtained in some cases.

After intensive investigations made for the purpose of developing a fungicide for surely controlling various soil borne plant diseases, the inventors have found that a mixture of compound A with PCNB or TPN shows a synergistic effect without giving any phytotoxicity on crops which is unexpected from the effect of the respective components. The present invention has been completed on the basis of this finding.

The weight ratio of compound A to PCNB is generally in the range of 1:5 to 5:1, preferably 1:1 to 5:1.

The weight ratio of compound A to TPN is generally in the range of 1:10 to 10:1, preferably 1:1 to 5:1.

The composition of the present invention may be used as it is or in the form of a mixture with an agricultural adjuvant which improves the effect or which stabilizes the composition depending on the purpose of the use. The composition may be used in the form of, for example, a dust, microgranules, granules, wettable powder or emulsion prepared by a method generally employed in the production of pesticides.

In the practical application, these various types of formulation may be used as they are or after dilution with water into a suitable concentration.

As the agricultural adjuvants herein used, there may be mentioned a carrier (diluent) as well as spreaders, emulsifiers, wetting agents, dispersing agents, binders and disintegrators etc.

As the liquid carriers, there may be mentioned aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and fatty acid esters, etc.

As the solid carriers, there may be mentioned clay, kaolin, talc, diatomaceous earth, silica, calcium carbonate, montmorillonite, bentonite, feldspar, quartz alumina and sawdust.

As the emulsifiers or dispersing agents, surfactants are generally used. They include anionic surfactants, cationic surfactants, nonionic surfactants and amphoteric surfactants such as sodium salts of higher alcohol sulfate, stearyltrimethylammonium chloride, polyoxyethylenealkylphenylethers and laurylbetaine, etc.

These formulations may be used either alone or in the form of a mixture with herbicides, insecticides, plant growth regulators, acaricides, germicides, soil disinfectants, soil modifying agents or nematocides. Further, they may be applied to the soil or locus of the fungi to be treated in the form of a mixture with a fertilizer or another agricultural and horticultural disinfectant.

When they are used in the above described forms, the concentrations of the compounds used as the effective components in the formulations are varied depending on the forms of the formulations and the agricultural adjuvants used. The concentration is, however, generally in the range of 2–95 wt. %.

And preferable content can be given differently for respective types of formulation. For example, in the case of dust, the content of effective components is 2 to 20%, that of adjuvants being 80 to 98%; in emulsion, the content of effective components is 5 to 40%, that of adjuvants being 60 to 95%; in flowable suspension concentrates, the content of effective components is 5 to 40%, that of adjuvants being 60 to 95%, while in wettable powder, the content of effective components is 20 to 80%, that of adjuvants being 20 to 80% and in granules and microgranules, the content of the effective components is 2 to 10%, that of adjuvants being 90 to 98%.

Then, detailed formulation examples of the present invention will be given below. The kinds of the adjuvants and the mixing ratios should not be limited to the ranges given in the examples but may extend over the ranges.

In the following examples, parts are given by weight.

FORMULATION EXAMPLE 1

Dust

7 Parts of compound A, 3 parts of PCNB, 40 parts of talc and 50 parts of clay were mixed together and pulverized to obtain a dust.

FORMULATION EXAMPLE 2

Dust

6 Parts of compound A, 4 parts of TPN, 40 parts of talc and 50 parts of clay were mixed together and pulverized to obtain a dust.

FORMULATION EXAMPLE 3

Wettable powder

50 Parts of compound A and 30 parts of PCNB were mixed with 15 parts of kaolin, 3 parts of sodium salts of higher alcohol sulfate and 2 parts of sodium polyacrylate and the mixture was finely pulverized to obtain a wettable powder.

FORMULATION EXAMPLE 4

Wettable powder

40 Parts of compound A and 30 parts of TPN were mixed with 25 parts of kaolin, 3 parts of sodium salts of higher alcohol sulfate and 2 parts of sodium polyacrylate and the mixture was finely pulverized to obtain a wettable powder.

FORMULATION EXAMPLE 5

Granules

3 Parts of previously finely pulverized compound A and 2 parts of previously finely pulverized PCNB were mixed with 93 parts of clay and 2 parts of polyvinyl alcohol. 15 Parts of water were added to moisten the mixture homogeneously. Then, the mixture was extrusion-molded into granules by means of a granulator. After dressing the granules in a dressing machine, granules having a diameter of 0.6–1 mm were obtained.

FORMULATION EXAMPLE 6

Granules

3 Parts of previously finely pulverized compound A and 2 parts of previously finely pulverized TPN were mixed with 93 parts of clay and 2 parts of polyvinyl alcohol. 15 Parts of water were added to moisten the mixture homogeneously. Then, the mixture was extrusion-molded into granules by means of a granulating machine. After dressing the granules in a dressing machine, granules having a diameter of 0.6–1 mm were obtained.

FORMULATION EXAMPLE 7

Microgranules

4 Parts of previously finely pulverized compound A and 4 parts of previously finely pulverized PCNB were homogeneously mixed with 11 parts of clay and 1 part of polyvinyl alcohol to obtain a concentrated powder mixture of the active ingredients. Separately, 80 parts of a non-absorbent coarse mineral powder of 74 to 105 micron size were placed in a proper mixer and then 20 parts of water were added thereto under rotation to moisten the former. The above powder mixture was added thereto to coat the latter with the former. The product was dried to obtain microgranules.

FORMULATION EXAMPLE 8

Microgranules

5 Parts of previously finely pulverized compound A and 5 parts of previously finely pulverized TPN were homogeneously mixed with 11 parts of clay and 1 part of polyvinyl alcohol to obtain a concentrated powder mixture of the active ingredients. Separately, 78 parts of a non-absorbent coarse mineral powder of 74 to 105 micron size were placed in a proper mixer and then 20 parts of water were added thereto under rotation to moisten the former. The above powder mixture was added thereto to coat the latter with the former. The product was dried to obtain microgranules.

EXPERIMENTAL EXAMPLE 1

Control test for clubroot of Chinese cabbage (caused by Plasmodiophora sp.)

Soil infested with Plasmodiophora brassicae was filled in biscuit pots having a diameter of 15 cm. Then, 10% dust containing the compounds of the present invention as prepared in the same manner as in Formulation Example 1 was added thereto in a predetermined amount and uniformly mixed with the soil. 15 Seeds of Chinese cabbage (variety: Taibyo 60-nichi) per pot were sowed. Four weeks thereafter, the seedlings of Chinese cabbage were grubbed out and the conditions thereof were examined.

The test results are shown in Table 1 in terms of a control value which is determined as follows:

Control value =

$$\frac{\text{Percentage of healthy seedlings in treated plots} - \text{Percentage of healthy seedlings in untreated plots}}{\text{Percentage of healthy seedlings in treated plots}} \times 100$$

Percentage of healthy seedling =

$$\frac{\text{Number of healthy seedlings}}{\text{Number of total seedlings checked}} \times 100$$

TABLE 1

|  | Compounds tested | Amount of effective component (g/pot) | Control value | Phytotoxicity |
| --- | --- | --- | --- | --- |
| Reference | Compound A | 1.0 | 75 | nil |
|  | Compound A | 0.5 | 42 | nil |
| Reference | PCNB | 1.0 | 54 | nil |
|  | PCNB | 0.5 | 20 | nil |
| Present invention | Compound A + PCNB | 0.5 + 0.5 | 92 | nil |
|  |  | 0.25 + 0.25 | 63 | nil |
|  |  | 1.0 + 0.25 | 98 | nil |
|  |  | 0.5 + 0.25 | 80 | nil |

EXPERIMENTAL EXAMPLE 2

Control test for clubroot of cabbage (caused by Plasmodiophora sp.)

Soil infested with Plasmodiophora brassicae was filled in biscuit pots having a diameter of 15 cm. Then, 10% dust containing the compounds of the present invention prepared in the same manner as in Formulation Example 2 was added thereto in a predetermined amount and uniformly mixed with the soil. 15 seeds of cabbage (variety: Kinshu) were sowed per pot.

Six weeks thereafter, the seedlings of cabbage were grubbed out and the conditions thereof were examined.

The test results are shown in Table 2 in terms of a control value which was determined in the same manner as in Experimental Example 1.

TABLE 2

| | Compounds tested | Amount of effective component (g/pot) | Control value | Phytotoxicity |
|---|---|---|---|---|
| Reference | Compound A | 1.0 | 75 | nil |
| | Compound A | 0.5 | 42 | nil |
| Reference | TPN | 1.0 | 50 | nil |
| | TPN | 0.5 | 18 | nil |
| Present invention | Compound A + TPN | 0.5 + 0.5 | 88 | nil |
| | | 0.25 + 0.25 | 60 | nil |
| | | 1 + 0.25 | 96 | nil |
| | | 0.5 + 0.25 | 74 | nil |

EXPERIMENTAL EXAMPLE 3

Control test for damping-off of cucumber (caused by Rhizoctonia sp.)

Field soil was filled in pots having a diameter of 12 cm and then 5 g of infested soil in which Rhizoctonia solani had been cultured was uniformly inoculated on the soil surface in each pot. The dust of the composition of the present invention prepared in the same manner as in Formulation Example 1 was added thereto in a predetermined amount and uniformly mixed with the soil. Then, 10 seeds of cucumber (variety: Oyashima) were sowed in each pot. They were allowed to grow in a greenhouse. Ten days after the sowing, the conditions were examined to determine the percentage of healthy seedlings.

Percentage of healthy seedlings =

$$\frac{\text{Number of healthy seedlings in each treated plot}}{\text{Number of germination in untreated and uninoculated plot}} \times 100$$

The test results are shown in Table 3 in terms of a control value which was determined in the same manner as in Experimental Example 1.

TABLE 3

| | Compound | Amount of effective component (g/pot) | Control value | Phytotoxicity |
|---|---|---|---|---|
| Reference | Compound A | 0.04 | 60 | nil |
| | Compound A | 0.02 | 35 | nil |
| Reference | PCNB | 0.04 | 78 | nil |
| | PCNB | 0.02 | 52 | nil |
| Present invention | Compound A + PCNB | 0.02 + 0.02 | 94 | nil |
| | | 0.01 + 0.01 | 74 | nil |
| | | 0.02 + 0.01 | 88 | nil |

EXPERIMENTAL EXAMPLE 4

Control test for damping-off of watermelon (caused by Rhizoctonia sp.)

Field soil was filled in pots having a diameter of 12 cm and then 5 g of infested soil in which Rhizoctonia solani had been cultured was uniformly inoculated on the soil surface in each pot. The dust of the composition of the present invention prepared in the same manner as in Formulation Example 2 was added thereto in a predetermined amount and uniformly mixed with the soil. Then, 10 seeds of watermelon (variety; Otome) were sowed in each pot. They were allowed to grow in a greenhouse. Fifteen days after the sowing, the conditions were examined to determine the percentage of healthy seedlings.

The percentage of seedlings were determined in the same manner as in Experimental Example 3.

The results are shown in Table 4 in terms of a control value which was determined in the same manner as in Experimental Example 1.

TABLE 4

| | Compound | Amount of effective component (g/pot) | Control value | Phytotoxicity |
|---|---|---|---|---|
| Reference | Compound A | 0.04 | 60 | nil |
| | Compound A | 0.02 | 35 | nil |
| Reference | TPN | 0.04 | 52 | nil |
| | TPN | 0.02 | 30 | nil |
| Present invention | Compound A + TPN | 0.02 + 0.02 | 84 | nil |
| | | 0.01 + 0.01 | 65 | nil |
| | | 0.02 + 0.01 | 75 | nil |

What is claimed is:

1. A fungicidal composition for agriculture and horticulture comprising at least one adjuvant in the range of 5–98% on the weight and, as an effective component, in the range of 2–95% on the weight, N-(1-n-butoxy-2,2,2-trichloroethyl) salicylamide and one member selected from the group consisting of (1) pentachloronitrobenzene in a weight ratio of 1:5–5:1 and (2) tetrachloroisophthalonitrile in a weight ratio of 1:1–5:1.

2. The fungicidal composition according to claim 1, wherein the ratio by weight of N-(1-n-butoxy-2,2,2-trichloroethyl) salicylamide to pentachloronitrobenzene is in the range of 1:1–5:1.

3. A method for controlling soil borne plant diseases caused by fungi which comprises applying to said fungi or locus thereof an effective amount of a mixture in the range of 2–95% on the weight of N-(1-n-butoxy-2,2,2-trichloroethyl) salicylamide and one compound selected from the group consisting of (1) pentachloronitrobenzene in a weight ratio of 1:5–5:1 and (2) tetrachloroisophthalonitrile in a weight ratio of 1:1–5:1 and an adjuvant in the range of 5–98% on the weight.

4. A method according to claim 3, wherein the ratio by weight of N-(1-n-butoxy-2,2,2-trichloroethyl) salicylamide to pentachloronitrobenzene is in the range of 1:1–5:1.